United States Patent
Sato et al.

(10) Patent No.: US 11,033,574 B2
(45) Date of Patent: Jun. 15, 2021

(54) METHOD FOR TREATING SCHIZOPHRENIA

(71) Applicant: MiZ Company Limited, Kamakura (JP)

(72) Inventors: Fumitake Sato, Kanagawa (JP);
Masatsugu Saito, Kanagawa (JP);
Ryosuke Kurokawa, Kanagawa (JP)

(73) Assignee: MIZ COMPANY LIMITED, Kamakura (JP)

( * ) Notice: Subject to any disclaimer, the term of this patent is extended or adjusted under 35 U.S.C. 154(b) by 13 days.

(21) Appl. No.: 16/521,192

(22) Filed: Jul. 24, 2019

(65) Prior Publication Data
US 2020/0030370 A1 Jan. 30, 2020

(30) Foreign Application Priority Data

Jul. 25, 2018 (JP) .............................. JP2018-139570

(51) Int. Cl.
*A61K 33/00* (2006.01)
*A61K 9/00* (2006.01)

(52) U.S. Cl.
CPC ................ *A61K 33/00* (2013.01); *A61K 9/00* (2013.01)

(58) Field of Classification Search
None
See application file for complete search history.

(56) References Cited

U.S. PATENT DOCUMENTS

2009/0035383 A1 2/2009 Ohta et al.

FOREIGN PATENT DOCUMENTS

WO WO 2007/021034 A1 2/2007

OTHER PUBLICATIONS

Molecular hydrogen: an overview of its neurobiological effects and therapeutic potential for bipolar disorder and schizophrenia, Ghanizadeh and Berk Medical Gas Research, http://www.medicalgasresearch.com/content/3/1/11, 2013, 3, pp. 1-6 (Year: 2013).*
Molecular hydrogen as a preventive and therapeutic medical gas: initiation, development and potential of hydrogen medicine, Pharmacology & Therapeutics, 144, 2014, pp. 1-11 (Year: 2014).*
Sleep and schizophrenia are intimately linked, retrieved from :<https://institute.progress.im/en/content/sleep-and-schizophrenia-are-intimately-linked>, Oct. 27, 2016 (Year: 2016).*
Ohta, "Molecular Hydrogen as a Novel Antioxidant: Overview of the Advantages of Hydrogen for Medical Applications", in Methods in Enzymology, vol. 555, Burlington: Academic Press, 2015, pp. 289-317.

* cited by examiner

*Primary Examiner* — Nannette Holloman
(74) *Attorney, Agent, or Firm* — Brinks Gilson & Lione

(57) ABSTRACT

A method for treating schizophrenia, comprising administering a composition containing a therapeutically effective amount of hydrogen gas to a subject in need of the treatment, by inhalation, is provided by the present invention.

8 Claims, No Drawings

METHOD FOR TREATING SCHIZOPHRENIA

This application claims priority to JP2018/139570 filed Jul. 25, 2018, the entire content of which is incorporated herein by reference.

TECHNICAL FIELD

The present invention relates to a therapeutic or preventive composition for schizophrenia. The present invention further relates to a method for treating or preventing schizophrenia, particularly to a method for treating or preventing schizophrenia, including administering hydrogen gas to a subject.

BACKGROUND ART

Recently, hydrogen gas (molecular hydrogen, $H_2$) has been introduced as a medical gas in the field of clinical medicine (NON PATENT LITERATURE 1). The effect brought about by hydrogen gas to the clinical medicine is presumably due to antioxidant activity, anti-apoptotic effect and anti-inflammatory effect that hydrogen gas has (PATENT LITERATURE 1).

Schizophrenia is a pathological condition in which an ability to integrate thinking, behavior and emotion toward a single purpose declines, in short, integration capability declines over a long term, and during which hallucination, delusion and extremely disorganized behavior are observed. The decreased abilities are rarely distinguishable from those observed in, e.g., depression, stay-at-home and adaptation disorder, in many cases. Thus, schizophrenia is definitively diagnosed based on symptoms such as hallucination and delusion. Hallucination and delusion relatively respond to drug therapy; however, longer-term treatment and support are subsequently required in order to improve the ability once decreased and promote rehabilitation into society. The incidence rate of schizophrenia during a lifetime is about 1% both in foreign countries and Japan (NON PATENT LITERATURE 2).

In the Diagnostic and Statistical Manual of Mental Disorders (DSM) published by the American Psychiatric Association, the diagnostic criteria for schizophrenia are described as follows: (1) two or more symptoms such as delusion, hallucination, disorganized conversation, seriously disorganized behavior (Examples: inappropriate clothes, frequent cry) or catatonic behavior and negative symptom are always present for a month or more, (2) a decline in social or occupational function, and (3) stigma of the disorder continues for at least 6 months (revised text of DSM-IV, DSM-IV-TR).

The drug therapy is carried out by using atypical antipsychotic (for example, risperidone, quetiapine, perospirone, olanzapine, aripiprazole, blonanserin, clozapine, paliperidone) as a first-choice drug.

CITATION LIST

Patent Literature

PTL 1: WO2007/021034

Non Patent Literature

NPL 1: Ohta S., et al., Methods Enzymol. 2015; 555: 289-317

NPL 2: Japanese Society of Psychiatry and Neurology, Website, https://www.jspn.or.jp/modules/activity/index.php?content_id=7 9

SUMMARY OF INVENTION

Technical Problem

The number of patients with schizophrenia is regarded as more than 20 million in the world; however, it cannot be said that the method for treating schizophrenia is sufficient. A safe and effective means for treating schizophrenia has been strongly desired.

Solution to Problem

The present inventors conducted studies in order to solve the aforementioned problems. As a result, they found that inhalation of hydrogen gas by the patients is effective for improving symptoms of schizophrenia. Based on the finding, the following inventions (1-1) to (1-9) were accomplished.

(1-1) A composition used for treating schizophrenia and containing hydrogen gas as an active ingredient, wherein hydrogen gas is inhaled by a subject.

(1-2) The composition according to (1-1), used for treating schizophrenia one or more years after onset.

(1-3) The composition according to (1-1) or (1-2), used for treating schizophrenia associated with insomnia.

(1-4) The composition according to any one of (1-1) to (1-3), wherein hydrogen gas is inhaled in the form of gas containing 3.0 vol % or more of hydrogen gas.

(1-5) The composition according to any one of (1-1) to (1-4), wherein hydrogen gas is inhaled in the form of gas containing 6.0 vol % or more of hydrogen gas.

(1-6) The composition according to any one of (1-1) to (1-5), wherein hydrogen gas is inhaled for 60 minutes or more per day.

(1-7) The composition according to any one of (1-1) to (1-5), wherein hydrogen gas is inhaled for 180 minutes or more per day.

(1-8) The composition according to any one of (1-1) to (1-7), used for improving symptoms in a stabilization phase of schizophrenia.

(1-9) The composition according to any one of (1-1) to (1-7), used for maintaining a stable phase of schizophrenia.

(2-1) A method for treating schizophrenia, comprising administering a composition containing a therapeutically effective amount of hydrogen gas to a subject in need of the treatment by inhalation.

(2-2) The method according to (2-1), wherein the subject is a patient with schizophrenia one or more years after onset.

(2-3) The method according to (2-1) or (2-2), in which the subject is a patient with schizophrenia associated with insomnia.

(2-4) The method according to any one of (2-1) to (2-3), wherein hydrogen gas is inhaled in the form of gas containing 3.0 vol % or more of hydrogen gas.

(2-5) The method according to any one of (2-1) to (2-4), wherein hydrogen gas is inhaled in the form of gas containing 6.0 vol % or more of hydrogen gas.

(2-6) The method according to any one of (2-1) to (2-5), wherein hydrogen gas is inhaled for 60 minutes or more per day.

(2-7) The method according to any one of (2-1) to (2-5), wherein hydrogen gas is inhaled for 180 minutes or more per day.

(2-8) The method according to any one of (2-1) to (2-7), for improving symptoms in a stabilization phase of schizophrenia.

(2-9) The method according to any one of (2-1) to (2-7), for maintaining a stable phase of schizophrenia.

Advantageous Effects of Invention

A method for treating schizophrenia and a method for alleviating symptoms of schizophrenia are provided by the present invention. The methods provided by the present invention have few side effects and are excellent as means to be applied over a long term.

DESCRIPTION OF EMBODIMENT

The present invention is used for treating schizophrenia. Schizophrenia is characterized by symptoms such as distortions in thinking, perception, emotions, language, sense of self and behavior from those of other persons and characterized in that the symptoms continue for one month or more. The treatment using the method of the present invention may be applied after the symptoms of schizophrenia are confirmed in subjects, or before firm diagnosis of schizophrenia and after confirmation of characteristic symptoms such as delusion and hallucination. The timing for initiating the treatment is not particularly limited.

The method of the present invention can be applied to patients with moderate or severe schizophrenia, for example, patients continuously having symptoms for one or more years, more specifically 2 or more years, further specifically 3 or more years from onset. The method of the present invention may be applied, for example, to patients with schizophrenia receiving a drug therapy. The composition of the present invention can be applied to patients with chronic schizophrenia.

The method of the present invention can be used in combination with a drug therapy. As a drug used in the drug therapy, antipsychotic drugs (atypical antipsychotic drug and typical antipsychotic drug) are mentioned. Examples of the atypical antipsychotic drug (second-generation antipsychotic drug) include risperidone, quetiapine, perospirone, olanzapine, aripiprazole, blonanserin, clozapine, paliperidone and asenapine. Examples of the typical antipsychotic drug (first-generation antipsychotic drug) include chlorpromazine, haloperidol and fluphenazine.

The antipsychotic drug can be administered in a dosage form such as an oral medicine, an intramuscular injection and an intravenous injection. The injection may be a long-acting injection or a fast-acting injection.

In an aspect of the present invention, there is provided a method for treating schizophrenia, including administering a composition containing a therapeutically effective amount of hydrogen gas to a subject by inhalation.

In an aspect of the present invention, the composition of the present invention can be used as a pharmaceutical composition. Owing to the therapeutic effect of the present invention, the dose of a drug to be used for a drug therapy for schizophrenia can be reduced and frequency of drug administration can be reduced. The composition of the present invention can be used for alleviating symptoms of insomnia and/or depressive symptoms of patients with schizophrenia.

The disease process of schizophrenia can be classified into four phases, i.e., an aura phase, an acute phase, a rest phase and a recovery phase. In the aura phase, degeneration such as prodrome of onset is sometimes observed and positive symptoms such as hallucination and delusion specific to schizophrenia are remarkably observed. In the rest phase, flattening of emotion and decreased motivation are sometimes observed, particularly reversion to the acute phase needs to be watched. In the recovery phase, symptoms gradually subside and recovery from a lethargy state is observed. The therapeutic effect of the present invention can contribute to alleviation of the symptoms in the acute phase, improvement of the symptoms in the rest period, and disappearance of the symptoms and stabilizing a disease state in the recovery period. In an aspect of the present invention, owing to the therapeutic effect of the present invention, the disease state in the recovery phase can be stably maintained while a drug therapy for schizophrenia is stopped. The pharmaceutical composition of the present invention can be also used for preventing onset of schizophrenia in the aura phase.

According to the guidelines of the Japanese Society of Neuropsychopharmacology, the process of schizophrenia is classified into an acute phase, a stabilization phase and a stable phase. It is interpreted that the acute phase is a period during which the disease state is active and unstable; the stabilization phase is a period during which the symptoms are improved, and the disease state comes to be stable; and the stable phase is a period during which the symptoms disappear and the disease state is stable. The stabilization phase and the stable phase are sometimes combined together rand referred to as a maintenance period. The therapeutic effect of the present invention can contribute to alleviation of symptoms in the acute phase, improvement of symptoms in the stabilization phase, and disappearance of symptoms and stability of the disease state in the stable phase. In an aspect of the present invention, owing to the therapeutic effect of the present invention, the disease state in the maintenance phase, particularly, in the stable phase, can be stably maintained while a drug therapy for schizophrenia is stopped.

The therapeutic effect of the present invention can contribute to alleviation of symptoms in the acute phase, improvement of symptoms in the stabilization phase, and disappearance of symptoms and stability of the disease state in the stable phase. In an aspect of the present invention, owing to the therapeutic effect of the present invention, the stable phase can be maintained while a drug therapy for schizophrenia is stopped.

In an aspect, the method of the present invention can be used for alleviating a symptom of schizophrenia selected from delusion, hallucination, disorganized conversation, seriously disorganized behavior (Examples: inappropriate clothes, frequent cry) catatonic behavior and negative symptoms. In an embodiment, the method of the present invention can be used for improving declined social or occupational function of patients with schizophrenia. In another embodiment, the method of the present invention can be applied to patients with schizophrenia associated with insomnia.

The composition of the present invention contains hydrogen gas as an active ingredient. In an embodiment of the present invention, hydrogen gas is used in the form of a gas containing hydrogen gas.

The gas containing hydrogen gas may be air containing hydrogen gas or a gas mixture of hydrogen gas and oxygen gas. The concentration of hydrogen gas in the gas containing hydrogen gas, although it is not particularly limited, is, for example, less than the lower detonation concentration of hydrogen gas, i.e., 18.3 vol % or less, for example, 0.5 vol % or more, 1.0 vol % or more, 0.5 to 18.3 vol %, more specifically, 1 to 10 vol %, more specifically 2 to 10 vol %, further more specifically 2 to 8 vol %, further more specifically 3 to 8 vol %, and further more specifically 6 to 8 vol %.

If the gas except hydrogen gas is air, the concentration of the air falls within the range of, for example, 81.7 to 99.5 vol %. If the gas except hydrogen gas is oxygen gas, the concentration of the oxygen gas falls within the range of, for example, 21 to 99.5 vol %. The gas containing hydrogen gas may contain two or more types of gases except hydrogen, such as air, oxygen gas, nitrogen gas and carbon dioxide gas. Hydrogen gas is flammable and explosive. In consideration of safety, hydrogen gas is preferably used in a concentration of an explosion limit or less.

The flow rate of hydrogen gas diluted to a safe concentration for use in inhalation can be, for example, 1 to 10 liters/minute and more specifically 2 to 4 liters/minute. In patients with hyperpnea, the flow rate can be 6 to 8 liters/minute. In an embodiment of the present invention, inhalation of the hydrogen gas composition can be carried out at a flow rate of 70 mL/minute or more, 140 mL/minute or more or 280 mL/minute in terms of amount of hydrogen contained in the composition.

The gas containing hydrogen gas is prepared so as to satisfy a predetermined hydrogen gas concentration, filled in a pressure vessel (for example, aluminum cans, pet bottles) and stored. Alternatively, the gas containing hydrogen gas may be prepared on site by use of a hydrogen gas supply device known in the art and used for inhalation.

The hydrogen gas supply device enables hydrogen gas generated by the reaction between a hydrogen-generating compound (for example, metallic aluminum) and water to mix with a dilution gas (for example, air, oxygen) in a predetermined ratio (Japanese Patent No. 5228142). Alternatively, the device enables hydrogen gas generated by electrolysis of water to mix with a dilution gas (Japanese Patent No. 5502973, Japanese Patent No. 5900688). In this manner, a gas containing hydrogen gas within the range of 0.5 to 18.5 vol % can be prepared.

In the present invention, hydrogen gas is administered to a subject by inhalation. The hydrogen gas administered is presumably absorbed through the mucous membrane in the airway and the lung until the gas administered reaches the lung. The hydrogen gas taken from, e.g., the lung is delivered to not only throughout the whole body via the blood but also individual tissues possibly by diffusion from the lung.

When hydrogen gas is inhaled, e.g., a mask-type material covering mouth and nose, or a nasal cannula, can be used.

The hydrogen gas taken in the body by inhalation is widely distributed in the brain, lung and muscle, and the cumulative hydrogen amount (AUC) is large compared to other administration methods such as oral administration, intraperitoneal administration and intravenous administration. If the case where a human takes hydrogen as a hydrogen-water drink is compared to the case where a human takes hydrogen by inhalation of hydrogen gas, most of hydrogen molecules taken from a hydrogen-water drink diffuse from the stomach and the intestinal tract and reach the tissue of the abdomen or organs; whereas part of the hydrogen molecules is absorbed from the intestinal wall and distributed to the tissues and organs of the whole body by the blood flow. In contrast, hydrogen gas inhaled is distributed by following routes: [1] hydrogen molecules are mixed with intake air, transferred to the lung tissue and diffused to the peripheral tissue; [2] hydrogen molecules are dissolved in the blood by gas exchange in the lung and transferred to the whole body; and [3] hydrogen molecules are directly transferred to the brain tissue through the nasal mucosa without passing through blood-brain barrier (BBB)

The gas having the aforementioned hydrogen concentration may be administered once or more times (for example, 2 to 3 times) per day. The administration period that can be set is, for example, a week or more, 2 weeks or more, 4 weeks or more, 2 months or more, 3 months or more, 6 months or more, a year or more, 2 years or more and 3 years or more. The administration time per dose that can be set, for example, 5 minutes or more, 10 minutes or more, 15 minutes or more, 20 minutes or more, 30 minutes or more, 40 minutes or more, one hour or more, 2 hours or more, 3 hours or more and 4 hours or more. The administration time may be a single continuous period or divided in a plurality of periods. The administration period and administration time may be appropriately set in consideration of the state of the subject. Inhalation of hydrogen gas does not provide a heavy burden on the health of a subject and few adverse events are reported. Because of this, inhalation of hydrogen gas is suitable for long-term treatment. In an embodiment of the present invention, a treatment using the method of the present invention can be continuously applied until the symptoms of schizophrenia are alleviated or disappear.

Hydrogen gas can be taken if a subject stays for a predetermined time in a space filled with a gas containing hydrogen gas. The barometric pressure in the space may be the standard atmospheric pressure (about 1.013 barometric pressure) or a larger pressure of 7 barometric pressure or less, for example, 1.02 barometric pressure to 7.0 barometric pressure, specifically 1.02 barometric pressure to 5.0 barometric pressure, more specifically 1.02 barometric pressure to 4.0 barometric pressure and further more specifically 1.02 barometric pressure to 1.35 barometric pressure. In order to promote in-vivo absorption of hydrogen in a subject, it is preferable to uptake hydrogen in a high pressure environment. For hydrogen uptake under pressure, a high pressure capsule designed so as to have a sufficient strength can be used.

EXAMPLES

Now, the present invention will be more specifically described by way of Reference Example and Example; however, the present invention is not limited to Examples.

Example 1

A patient (30s, woman) who developed schizophrenia 13 years ago and have received a drug therapy for 12 years and 10 months, was allowed to continuously inhale hydrogen gas having a concentration 3.0 to 6.0% by use of two types of hydrogen generators, (MHG-2000 and MHG-2000a, manufactured by Miz Co., Ltd.). At the initiation of hydrogen gas inhalation, a drug therapy with Abilify (intramuscular injection, 400 mg/month, once) and Lexotan tablets (oral administration, 6 mg/day, 3 times per day) was carried out.

Conditions of hydrogen gas inhalation were as follows:
For 40 days after initiation of inhalation: once per day, 70 mL/minute;
The subsequent 1 month: 2 hours per day, 70 mL/minute, hydrogen gas concentration: 3.0 to 4.0%;
The subsequent 4 months: 2 hours per day, 140 mL/minute, hydrogen gas concentration: 6.0 to 7.0%;
The subsequent 4 months: 6 hours per day, 280 mL/minute, hydrogen gas concentration: 6.0 to 7.0% (two hydrogen inhalers were used).

After initiation of hydrogen inhalation, a consecutive symptom, hallucination, disappeared. Ten days after initiation of hydrogen inhalation, administration of the oral medicine was terminated (9 months). Injection of a medicine (once a month) was continued for 8 months even after initiation of hydrogen inhalation, and thereafter, stopped.

At initiation of inhalation, the patient took a sleeping pill (brotizolam tablet, 0.25 mg/day) every day; however, about 2 months after initiation of inhalation, the day started to come when the patient fell asleep without taking the sleeping pill. About 6 months after initiation of inhalation, use of the sleeping pill was stopped.

About 10 months after initiation of hydrogen inhalation, the patient was in the recovery phase, the disease-state was stably maintained in the period during which hydrogen inhalation was continued.

Thereafter, the patient was allowed to inhale hydrogen gas (6.0 to 7.0%, 280 mL/minute) for 6 hours/day, continuously for 9 months. According to medical examination during an office visit, the disease state was stable. As the results of the examination in January of 2019, the value of the patient was the same as in a healthy person.

In March of 2019, the patient stopped inhalation of hydrogen gas; however, no recurrence occurred.

What is claimed is:

1. A method for preventing or improving schizophrenia, comprising:
   administering a composition containing an effective amount of hydrogen gas to a subject by inhalation.

2. The method according to claim 1, wherein the subject is a patient with schizophrenia one or more years after onset.

3. The method according to claim 1, wherein hydrogen gas is inhaled for 60 minutes or more per day.

4. The method according to claim 1, wherein preventing or improving schizophrenia comprises alleviating at least one symptom of schizophrenia, wherein the symptom is delusion, hallucination, disorganized conversion, seriously disorganized behavior, catatonic behavior, negative symptoms, declined social or occupational function, insomnia, and depressive symptoms.

5. The method according to claim 1, wherein the administration of the composition, when in conjunction with a drug therapy, allows for reducing the dose amount of a drug used for preventing or improving schizophrenia, or reducing the frequency of administration of a drug used for preventing or improving schizophrenia.

6. The method according to claim 1, wherein preventing or improving schizophrenia comprises at least one of:
   alleviating at least one symptom of schizophrenia in an acute phase,
   improving at least one symptom of schizophrenia in a stabilization phase, and
   disappearing of at least one symptom and stabilizing of disease state of schizophrenia in the stable phase.

7. The method according to claim 1, wherein the composition is inhaled in the form of gas containing less than about 18.3% of hydrogen gas.

8. The method according to claim 1, wherein the composition is prepared using a hydrogen gas supply device.

* * * * *